United States Patent
Grisoni

(10) Patent No.: US 7,067,153 B2
(45) Date of Patent: Jun. 27, 2006

(54) MICROCAPSULE POWDER

(75) Inventor: Philippe Grisoni, Bey sur Seille (FR)

(73) Assignee: Cognis France S.A., Boussens (FR)

( * ) Notice: Subject to any disclaimer, the term of this patent is extended or adjusted under 35 U.S.C. 154(b) by 312 days.

(21) Appl. No.: 10/381,553

(22) PCT Filed: Sep. 18, 2001

(86) PCT No.: PCT/EP01/10765

§ 371 (c)(1),
(2), (4) Date: Mar. 25, 2003

(87) PCT Pub. No.: WO02/24319

PCT Pub. Date: Mar. 28, 2002

(65) Prior Publication Data

US 2003/0180369 A1    Sep. 25, 2003

(30) Foreign Application Priority Data

Sep. 25, 2000 (FR) .................................. 00 12168

(51) Int. Cl.
- *A61K 9/16* (2006.01)
- *A61K 9/48* (2006.01)
- *A61K 9/66* (2006.01)
- *A61K 9/52* (2006.01)
- *A61K 9/14* (2006.01)
- *A01N 25/28* (2006.01)

(52) U.S. Cl. .................. 424/490; 424/417; 424/451; 424/455; 424/457; 424/489; 424/497; 424/498; 424/604; 514/938; 514/951; 514/963; 514/965; 514/492

(58) Field of Classification Search ................ 424/19, 424/417, 451, 455, 457, 489, 490, 497, 498, 424/604; 514/938, 951, 963, 965, 492
See application file for complete search history.

(56) References Cited

U.S. PATENT DOCUMENTS

| | | | |
|---|---|---|---|
| 4,164,563 A | 8/1979 | Chang | |
| 4,652,441 A * | 3/1987 | Okada et al. | 424/497 |
| 5,356,617 A | 10/1994 | Schlossman | |
| 5,705,169 A | 1/1998 | Stein et al. | |
| 5,730,960 A | 3/1998 | Stein et al. | |
| 5,780,056 A * | 7/1998 | Akamatsu et al. | 424/464 |
| 5,945,091 A | 8/1999 | Habeck et al. | |
| 5,948,417 A | 9/1999 | Mori | |
| 5,962,663 A | 10/1999 | Wachter et al. | |
| 6,001,382 A * | 12/1999 | Levy | 424/405 |
| 6,193,960 B1 | 2/2001 | Metzger et al. | |
| 2003/0180235 A1 | 9/2003 | Grisoni et al. | |

FOREIGN PATENT DOCUMENTS

| | | |
|---|---|---|
| DE | 41 22 591 C1 | 7/1991 |
| DE | 44 42 987 A1 | 6/1996 |
| DE | 195 37 001 A1 | 3/1997 |
| DE | 197 12 978 A1 | 10/1997 |
| DE | 197 12 033 A1 | 9/1998 |
| DE | 198 45 246 A1 | 6/1999 |
| EP | 0 622 451 B1 | 11/1994 |
| EP | 0 659 403 B1 | 6/1995 |
| EP | 0 693 471 B1 | 1/1996 |
| EP | 0 694 521 B1 | 1/1996 |
| EP | 0 818 450 B1 | 1/1998 |
| EP | 99 122 906 | 11/1999 |
| EP | 1 064 910 A1 | 1/2001 |
| EP | 1 101 527 A1 | 5/2001 |
| FR | 2 701 266 | 8/1994 |
| FR | 2 775 441 | 9/1999 |

OTHER PUBLICATIONS

J.Falbe, "Surfactants in Consumer Products", Springer Verlag, Berlin, (1987), pp. 54-124.

J.Falbe, "Katalysatoren, Tenside und Mineralöladditive" (Catalysts, Surfactants and Mineral Oil Addivites), Thieme Verlag, Stuttgart, (1978), pp. 123-217.

P.Finkel, "Formulierung kosmetischer Sonnenschutzmittel", SÖFW-Journal, 122, (1996), pp. 543-546 & 548.

"Kosmetische Färbemittel", Farbstoffkommission der Deutschen Forschungsgemeinschaft, Verlag Chemie, Weinheim, (1984), pp. 81-106.

"Ullmann's Encyclopedia of Industrial Chemistry", 5th Ed., vol. A6, Weinheim, Verlag Chemie, (1986), pp. 231-332.

(Continued)

*Primary Examiner*—John Pak
*Assistant Examiner*—Ernst Arnold
(74) *Attorney, Agent, or Firm*—John F. Daniels; Daniel S. Ortiz

(57) ABSTRACT

A process for making hydrophobicized powders of micro- and/or nanocapsules involving the steps of: (a) providing an aqueous polymer solution containing at least one active ingredient and at least one hydrophilic polymer; (b) providing an oil component heated to a temperature above a gel point of the aqueous polymer solution; (c) dispersing (a) in (b) in the presence of a water-in-oil emulsifier to form a dispersion; (d) cooling the dispersion to a temperature below the gel point of the aqueous polymer solution to form micro- and/or nanocapsules containing the active ingredient encapsulated therein; (e) harvesting the micro- and/or nanocapsules from the dispersion; and (f) contacting the micro- and/or nanocapsules with an oil-absorbing auxiliary ingredient.

10 Claims, No Drawings

OTHER PUBLICATIONS

Gesslein et al., "Chitosan, a gift from the sea", HAPPI, vol. 27, (Oct. 1990), pp. 57 & 59.

O. Skaugrud, "Chitosan—New Biopolymer For Cosmetics & Drugs", Drug Cosm. Ind., vol. 148, (May, 1991), pp. 24, 26 & 30.

Onsoyen, et al., "Adding Benefits to Cosmetic Formulations by Tailormade Chitosans", Seifen-Öle-Fette-Wachse, vol. 117, (1991), pp. 633-637.

Sannan, et al., "Studies on Chitin, 2*", Markromol. Chem., vol. 177, (1976), pp. 3589-3600.

* cited by examiner

MICROCAPSULE POWDER

BACKGROUND OF THE INVENTION

This application is a 371 of PCT/EP01/10765 filed Sep. 18, 2001.

This invention relates generally to the encapsulation of active substances and, more particularly, to hydrophobicized powders consisting of micro- and/or nanocansules, to a process for their production and to their use in cosmetic and pharmaceutical preparations.

"Microcapsules" are understood to be spherical aggregates with a diameter of about 1 to about 5,000 μm and "nanocapsules" similar aggregates with a diameter below 1 μm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") which, as microparticles, may be additionally coated with film-forming polymers. Transitions between micro- or nanoparticles in which substances are encapsulated in a membrane (reservoir system) and micro- or nanoparticles in which the active substances are dispersed or dissolved in the carrier matrix (matrix system) arise out of the particular production process. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone.

Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicerin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

Reference is also made in this connection to German patent application DE 19712978 A1 (Henkel) which describes chitosan microspheres obtained by mixing chitosans or chitosan derivatives with oil components and introducing the resulting mixtures into alkalized surfactant solutions. In addition, the use of chitosan as an encapsulating material for tocopherol is known from German patent application DE 19756452 A1 (Henkel). Patent Application EP 99 122 906 relates to microcapsules with mean diameters of 0.1 to 500, preferably 25 to 250 and more particularly 50 to 100 μm which consist of a membrane material of starch and chitosans.

The micro- and nanocapsules produced in different ways may then be converted into a powder-form end product by drying in the form of freeze-drying or fluidized-bed drying or by the removal of water (FR 2775441 B1 and EP 99 122 906). In many cases, however, further processing such as this involves complicated, expensive and time-consuming processes and often leads to premature destruction of the micro- and nanocapsules. Since the microcapsules have hydrophilic surface properties, they are often difficult to incorporate in lipophilic preparations.

So-called dispersion aids (colloidal silicon), which contribute towards optimizing the flowability of the powders, are only used after the powders have been isolated. An advantage of similar formulations used in cosmetics is the regulation of fat-absorbing as opposed to drying-out properties (U.S. Pat. No. 5,948,417). U.S. Pat. No. 5,356,617 describes how the unsatisfactory processing of hydrophilic pigments can be improved by the production of microparticles from organic polymer, inorganic pigments and a binder. Even oily substances and lipophilic carriers can be converted for better processing into powders which are then readily incorporated in cosmetic preparations (EP 0 659 403 and U.S. Pat. No. 4,164,563). However, the use of micro- and/or nanocapsules raises greater processing problems.

The active principles are released from the microcapsules by mechanical, thermal, chemical or enzymatic destruction of the membrane or by diffusion, normally during the use of the preparations containing the microcapsules. Disadvantages in this regard are that the microcapsules do not allow controlled release of the active principles from their interior at all or only to an inadequate extent and that the capsules lack stability in the presence of surfactants, especially anionic surfactants, salts or mechanical loads.

Accordingly, the problem addressed by the present invention was to provide a stable powder-form formulation consisting of hydrophilically encapsulated active substances and auxiliaries which would be easy to incorporate in water-free formulations. The powder would be produced by simple, economical processes. In addition, release behavior would be able to be controlled and the formulation would be guaranteed a long storage life.

DESCRIPTION OF THE INVENTION

The present invention relates to hydrophobicized powders consisting of micro- and/or nanocapsules obtainable by (a) dispersing an aqueous solution of at least one polymer in an oil in the presence of a w/o emulsifier at a temperature above the gel point of the polymer solution,
(b) cooling the dispersion while stirring to a temperature below the gel point,
(c) isolating the micro- and/or nanocapsules formed by decantation and
(d) adding an oil-absorbing auxiliary to the oily dispersion obtained.

It has surprisingly been found that hydrophobicized powders can be produced simply by mixing an oily dispersion of micro- and/or nanocapsules with oil-absorbing auxiliaries and that this formulation represents a stable powder with a high content of water-soluble active substances. The layer of the adhering oil-absorbing auxiliaries hydrophobicizes the hydrophilic micro- and/or nanocapsules and protects them against premature hydration and oxidation. The formulation is easy to incorporate in water-free preparations and is distinguished by high storage stability without any agglomeration of the hydrophilic micro- and/or nanocapsules. In addition, the release of the encapsulated active substances can be controlled by varying the type and quantity of the oil-absorbing auxiliary.

The present invention also relates to a process for the production of hydrophobicized powders consisting of micro- and/or nanocapsules, in which
(a) a heated aqueous solution of at least one polymer is dispersed in an oil in the presence of a w/o emulsifier at a temperature above the gel point of the polymer solution,
(b) the dispersion is cooled while stirring to a temperature below the gel point,
(c) the micro- and/or nanocapsules formed are isolated by decantation and
(d) an oil-absorbing auxiliary is added to the oily dispersion obtained, and to the use of the hydrophobicized powders in cosmetic and/or pharmaceutical preparations and detergents.

Micro- and/or Nanocapsules

The micro- and/or nanocapsules present in the hydrophobicized powders according to the invention are formed during the cooling of a polymer-containing w/o emulsion. After decantation, the oily dispersion present after cooling has a solids content of 85 to 95% by weight consisting of hydrophilic micro- and/or nanocapsules and 5 to 15% by weight of the oil used in the outer phase. The micro- and/or nanocapsules have a mean diameter of 0.1 to 500 μm, preferably 25 to 100 μm and more particularly 10 to 50 μm. Particles smaller than 50 μm in diameter in particular resemble the particle size of many powder formulations in decorative cosmetics and may therefore be inconspicuously incorporated.

Polymers

Hydrophilic materials are mainly used as polymers for forming the capsule matrix. The membrane may consist of natural, semisynthetic or synthetic materials. Natural membrane materials are, for example, gum arabic, agar agar, agarose, carrageen, maltodextrins, alginic acid and salts thereof, for example sodium or calcium alginate, fats and fatty acids, cetyl alcohol, collagen, chitosan, lecithins, gelatin, gluten, albumin, shellac, polysaccharides, such as starch or dextran, polypeptides, protein hydrolyzates, sucrose, xanthan or gellan gum. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and phthalate, methyl cellulose and carboxymethyl cellulose, and starch derivatives, more particularly starch ethers and esters, and stearates. Synthetic membrane materials are, for example, polymers, such as polyacrylates, polyamides, polyvinyl alcohol, polyglycolates, polyoxyethylenes, polylactates, polyglutamates, polyimides or polyvinyl pyrrolidone.

Oil Components

Oil components suitable for use as the outer phase in the production of the micro- and/or nanocapsules include vegetable, animal, semisynthetic and synthetic oils, for example Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons such as, for example, squalane, squalene or dialkyl cyclohexanes.

Oil Absorbers

The oil-absorbing auxiliary d) is used in quantities of 5 to 35% by weight, preferably in quantities of 10 to 30% by weight and more particularly in quantities of 15 to 25% by weight, based on the quantity of hydrophobicized powder. It may be selected from any cosmetically and pharmaceutically compatible substances such as, for example, organic and inorganic pigments, dimethicone, dimethicone cross polymers, starch, methacrylate compounds and acrylate copolymers, polymethyl methacrylates, silicates, magnesium stearate, zinc stearate, magnesium carbonate.

Active Substances for Cosmetic and Pharmaceutical Applications

Typical examples of active substances used in cosmetic and pharmaceutical preparations are plant extracts, active substances with antibacetrial, anti-acne and keratolytic properties, surfactants, cosmetic oils, pearlizing waxes, stabilizers, biogenic agents, vitamins, deodorants, antiperspirants, anti-dandruff agents, UV protection factors, antioxidants, preservatives, insect repellents, self-tanning agents, tyrosine inhibitors (depigmenting agents), perfume oils and dyes.

Anionic, nonionic, cationic and/or amphoteric or zwitterionic surfactants may be encapsulated as surfactants. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monolyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl-(ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineral-öladditive (Catalysts, Surfactants and Mineral Oil Additives)", Thieme Verlag, Stuttgart, 1978, pages 123–217.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, koji acid, amino acids, ceramides, pseudoceramides, essential oils, plant extracts and vitamin complexes.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors,
auxiliaries in the form of, for example, thickeners or complexing agents and/or
nonaqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox, ketoconazole and zinc pyrithione.

Examples of UV protection factors are organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP 0 818 450 A1, or Dioctyl Butamido Triazine (Uvasorb® HEB);

propane-1,3-diones such as, for example, 1-(4-tert.butylphenyl)-3-(4'-methoxyphenyl)-propane-1,3-dione;

ketotricyclo(5.2.1)decane derivatives, as described in EP 0 694 521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789), 1-phenyl-3-(4'-isopropylphenyl)-propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to µmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), liponic acid, tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active principles suitable for the purposes of the invention (salts, esters, ethers, sugars, nucleotides, nucleosides, peptides and lipids).

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetyl-aminopropionate. A suitable self-tanning agent is dihydroxyacetone. Tyrosine inhibitors, which prevent the formation of melanin and are used in depigmenting formulations, are for example arbutin, koji acid, coumaric acid and ascorbic acid (vitamin C)

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These active principles may also be present in the capsules solely for aesthetic reasons, i.e are not intended for controlled release.

Active Principles for Detergent Applications

Where microcapsules are used in the field of detergents, particularly laundry detergents, it is again desirable to prevent the various ingredients from coming into contact with one another. Thus, it is appropriate to encapsulate chemically sensitive substances, such as perfume oils or optical brighteners for example, in order to safeguard their activity, for example in chlorine or peroxide bleach liquors, even in the event of prolonged storage. However, use is also made of the fact that the bleaching of textiles generally takes place during rather than at the beginning of the washing process, the release delayed by mechanical action on the microcapsules ensuring that the bleaching agents develop their full effect at the right time. Accordingly, active principles to be encapsulated for detergent applications include, above all, bleaching agents, bleach activators, enzymes, redeposition inhibitors, optical brighteners and (chlorine- and peroxide-stable) perfumes and dyes.

Among the compounds yielding hydrogen peroxide in water which are used as bleaching agents, sodium perborate tetrahydrate and sodium perborate monohydrate are particularly important. Other suitable bleaching agents are, for example, peroxycarbonate, citrate perhydrates and salts of peracids, such as perbenzoates, peroxyphthalates or diperoxydodecanedioic acid. They are normally used in quantities of 8 to 25% by weight. Sodium perborate monohydrate is preferred and is used in quantities of 10 to 20% by weight and preferably in quantities of 10 to 15% by weight. By virtue of its ability to bind free water to form the tetrahydrate, it contributes towards increasing the stability of the detergent.

Examples of suitable bleach activators are N-acyl and O-acyl compounds which form organic peracids with hydrogen peroxide, preferably N,N'-tetraacylated diamines, also carboxylic anhydrides and esters of polyols, such as glucose pentaacetate. The bleach activator content of bleach-containing compositions is in the usual range, i.e. preferably between 1 and 10% by weight and more preferably between 3 and 8% by weight. Particularly preferred bleach activators are N,N,N',N'-tetraacetyl ethylenediamine and 1,5-diacetyl-2,4-dioxohexahydro-1,3,5-triazine.

Suitable enzymes are those from the class of proteases, lipases, amylases, cellulases and mixtures thereof. Enzymes obtained from bacterial strains or fungi, such as *Bacillus subtilis*, *Bacillus licheniformis* and *Streptomyces griseus*, are particularly suitable. Proteases of the subtilisin type are preferably used, proteases obtained from *Bacillus lentus* being particularly preferred. They may be used in quantities of about 0.2 to about 2% by weight. The enzymes may be adsorbed onto supports and/or encapsulated in membrane materials to protect them against premature decomposition. In addition to the monohydric and polyhydric alcohols and the phosphonates, the compositions may contain other enzyme stabilizers. For example, 0.5 to 1% by weight of sodium formate may be used. It is also possible to use proteases which are stabilized with soluble calcium salts and which have a calcium content of preferably about 1.2% by weight, based on the enzyme. However, it is of particular advantage to use boron compounds, for example boric acid, boron oxide, borax and other alkali metal borates, such as the salts of orthoboric acid ($H_3BO_3$), metaboric acid ($HBO_2$) and pyroboric acid (tetraboric acid $H_2B_4O_7$).

Suitable redeposition inhibitors are water-soluble, generally organic colloids, for example the water-soluble salts of polymeric carboxylic acids, glue, gelatine, salts of ether carboxylic acids or ether sulfonic acids of starch or cellulose or salts of acidic sulfuric acid esters of cellulose or starch. Water-soluble polyamides containing acidic groups are also suitable for this purpose. Soluble starch preparations and other starch products than those mentioned above, for example degraded starch, aldehyde starches, etc., may also be used. Polyvinyl pyrrolidone is also suitable. However, cellulose ethers, such as carboxymethyl cellulose, methyl cellulose, hydroxyalkyl cellulose, and mixed ethers, such as methyl hydroxyethyl cellulose, methyl hydroxypropyl cellulose, methyl carboxymethyl cellulose and mixtures thereof, and polyvinyl pyrrolidone are also preferably used, for example in quantities of 0.1 to 99% by weight and preferably 1 to 5% by weight, based on the composition.

Derivatives of diaminostilbene disulfonic acid or alkali metal salts thereof may be used as optical brighteners. Suitable optical brighteners are, for example, salts of 4,4'-bis-(2-anilino-4-morpholino-1,3,5-triazinyl-6-amino)-stilbene-2,2'-disulfonic acid or compounds of similar structure which, instead of the morpholino group, contain a diethanolamino group, a methylamino group, an anilino group or a 2-methoxyethylamino group. Brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)-4'-(2-sulfostyryl)-diphenyl, may also be present. Mixtures of the brighteners mentioned above may also be used. A particularly preferred dye is Tinolux® (a product of Ciba-Geigy).

Examples of perfumes stable to active chlorine are: citronellol (3,7-dimethyl-6-octen-1-ol), dimethyl octanol (3,7-dimethyl-1-octanol), hydroxycitronellol (3,7-dimethyloctane-1,7-diol), mugol (3,7-dimethyl-4,6-octatrien-3-ol), myrcenol (2-methyl-6-methylene-7-octen-2-ol), terpinolene (p-mentho-1,4-(8)-diene), ethyl-2-methyl butyrate, phenyl propyl alcohol, galaxolide (1,3,4,6,7,8-hexahydro-4,6,6,7,8,8-hexamethyl cyclopental-2-benzopyran), tonalide (7-acetyl-1,1,3,4,4,6-hexamethyl tetrahydronaphthalene), rose oxide, linalol oxide, 2,6-dimethyl-3-octanol, tetrahydroethyl linalool, tetrahydroethyl linalyl acetate, o-sec.-butyl cyclohexyl acetate and isolone diphorenepoxide and also isoborneal, dihydroterpineol, isobornyl acetate, dihydroterpenyl acetate). Other suitable perfumes are the substances mentioned columns 3 and 4 of European patent application EP 0622451 A1 (Procter & Gamble).

Besides inorganic types, such as iron or bismuth oxides for example, suitable pigments are, above all, green chlorophthalocyanines (Pigmosol® Grün, Hostaphine® Grün), yellow Solar Yellow BG 300 (Sandoz), blue chlorophthalocyanine (Hostaphine® Blau) or Cosmenyl® Blau.

Chitosans

Chitosans are biopolymers which belong to the group of hydrocolloids. Chemically, they are partly deacetylated chitins differing in their molecular weights which contain the following—idealized—monomer unit:

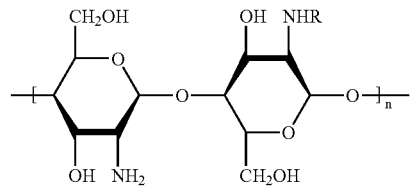

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations (cf. Ullmann's Encyclopedia of Industrial Chemistry, 5th Ed., Vol. A6, Weinheim, Verlag Chemie, 1986, pages 231–332). Overviews of this subject have also been published, for example, by B. Gesslein et al. in HAPPI 27, 57 (1990), O. Skaugrud in Drug Cosm. Ind. 148, 24 (1991) and E. Onsoyen et al. in Seifen-Öle-Fette-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, deminerlized by addition of mineral acids and, finally, deacetylated by addition of strong bases, the molecular weights being distributed over a broad spectrum. Corresponding processes are known, for example, from Makromol. Chem. 177, 3589 (1976) or French patent application FR 2701266 A. Preferred types are those which are disclosed in German patent applications DE 4442987 A1 and DE 19537001 A1 (Henkel) and which have an average molecular weight of 10,000 to 500,000 dalton or 800,000 to 1,200,000 dalton, a Brookfield viscosity (1% by weight in glycolic acid) below 5,000 mPas, a degree of deacetylation of 80 to 88% and an ash content of less than 0.3% by weight. In the interests of better solubility in water, the chitosans are generally used in the form of their salts, preferably as glycolates.

Production of the Microcapsules

Basically, any processes for the production of micro- and/or nanocapsules in which the capsules formed are present as a dispersion with an oil component in the outer phase, which may then be mixed with the oil-absorbing auxiliary, may be used. Particular emphasis is placed on the w/o emulsion method combined with gelation by temperature reduction.

To produce the hydrophobicized powders according to the invention, an aqueous solution or dispersion is initially prepared by thorough mixing of active substances and auxiliaries. The hydrophilic polymers used to form the matrix are dissolved in the solution or dispersion by heating beyond their gel point or, if necessary, are dissolved while heating in the aqueous solvent and combined with the heated solution of the other active substances and auxiliaries. If necessary, other hydrophilic solvents, for example ethanol or isopropanol, may also be added to the aqueous solution besides water. This aqueous solution or dispersion is then dispersed with intensive stirring in an oil heated to beyond the gel temperature of the matrix-forming polymer. Up to this step, all operations take place above the gel temperature of the hydrophilic polymer. After homogeneous emulsification, the emulsion is cooled to a temperature below the gel point of the hydrophilic polymer, resulting in the formation of an oily dispersion with a solids content of micro- and/or nanocapsules and an outer phase of the oil. To isolate the micro- and/or nanocapsules, excess oil is slowly decanted off so that the the dispersion obtained has an oil content of about 20 to 2% by weight and preferably 10 to 5% by weight.

The adhering oil layer is then adsorbed by intensive mixing of the dispersion with an oil-absorbing powder-form auxiliary. Mixing is carried out with commercially available powder mixers until a homogeneous powder mixture is obtained.

On average, the micro- and/or nanocapsules present in the powder have a diameter of 0.1 to 500 µm, preferably 50 to 100 µm and more particularly 10 to 50 µm. The particle diameter is determined by laser diffractometry (Malvern Instruments), the measurements giving a volume distribution.

In the encapsulation of active substances, the micro- and/or nanocapsules may be charged with 0.1 to 50% by weight, preferably 1 to 25% by weight and more particularly 5 to 10% by weight of active substance.

Commercial Applications

Micro- and/or nanocapsules in the form of the hydrophobicized powder may be used for various purposes. Their main function is the controlled released and protection of the encapsulated substances. This protective function includes oxidation by atmospheric oxygen, the protection of hygroscopic materials, UV protection and also the separation of mutually incompatible ingredients which can be separately stored in this way. The stability of the processed ingredients in particular is thus increased. In addition, it may be intended to mask ingredients where odor, taste and/or appearance are to be concealed.

Basically, the choice of the active substances encapsulated in the new microcapsules is not critical. Preferably, they are substances which are only released by mechanical destruction of the microcapsules. In cases such as these, the function of the microcapsules is to prevent contact between the surrounding environment and the active substance and hence a chemical reaction or degradation. It may be that the substances encapsulated in the capsules are not to be released at all and are merely intended to give the preparation an aesthetic appearance. This is often the case, for example, with dyes. It is of course clear that these forms of use may also exist alongside one another. In particular, it is possible, for example, to encapsulate a perfume for subsequent release together with a pigment which gives the capsules a particular appearance.

For processing in cosmetic and/or pharmaceutical preparations, it is often of advantage for the micro- and/or nanocapsules to be present in powder form. The powder formulations according to the invention may be charged with various active principles which they are capable of releasing with delay and under mechanical pressure. They are distinguished from known formulations by greater stability, particularly in the event of further mechanical processing. Accordingly, the hydrophobicized powders may also be used in laundry detergents, dishwasher detergents, cleaners and conditioners and also for the production of foods. The powders may normally be used in quantities of 0.01 to 100% by weight, preferably in quantities of 0.1 to 50% by weight and more preferably in quantities of 1 to 25% by weight, based on the preparations. The powders according to the invention are preferably used for the production of cosmetic products such as, for example, hair shampoos, hair lotions, foam baths, shower baths, creams, gels, lotions, alcoholic and aqueous/alcoholic solutions, emulsions, wax/fat-based compositions, stick preparations, powders and, more particularly, decorative cosmetic preparations such as, for example, makeup, rouge, lipstick, cajal, eye shadow, mascara and nail varnish. The hydrophobicized powders may be excellently incorporated in particular in water-free preparations which contain less than 5% by weight, preferably less than 3% by weight and more particularly less than 1% by weight of water. These preparations may contain as further auxiliaries and additives mild surfactants, oil components, emulsifiers, superfatting agents, pearlizing waxes, consistency factors, thickeners, polymers, silicone compounds, fats, waxes, lecithins, phospholipids, stabilizers, biogenic agents, deodorants, antiperspirants, antidandruff agents, film formers, swelling agents, UV protection factors, antioxidants, hydrotropes, preservatives, insect repellents, self-tanning agents, tyrosine inhibitors (depigmenting agents), solubilizers, perfume oils, dyes and the like. The majority of these substances are also potential active principles with which the microcapsules may be charged and have already been described in detail in this chapter.

EXAMPLES

Example 1

1a: Production of the hydrophilic particles

| | | | % by weight |
|---|---|---|---|
| Phase A | | | |
| 1 Agar | * | | 1.50 |
| 2 Preservative | | | q.s. |
| 3 Titanium dioxide | | | 3.00 |
| 4 Photonyl LS ® | ** | | 30.00 |
| 5 Water | | | to 100.0 |
| Phase B | | | |
| 6 Cetiol ® OE | Dicaprylyl Ether | | 99.50 |
| 7 Dehymuls ® PGPH | Polyglyceryl-2-Dipolyhydroxystearate | | 0.50 |

\* Granulated Agar-Agar produced by Merck, Darmstadt, Art. No.: 1.01614
\*\* Commercial product of Laboratoires Sérobiologiques consisting of arginine, sodium adenosine triphosphate, mannitol, pyridoxine HCl, RNA, histidine HOl, phenylalanine and tyrosine Agar is dissolved in preserved water at 90° C. and then cooled to 75° C. Titanium dioxide and Photonyl® LS are then added with stirring. the solution is kept at 55° C. Cetiol® OE and Dehymuls® PGHG are mixed and heated to 40–42° C. One part of phase A is dispersed in 3.3 parts of phase B by stirring with an Ultra-Turrax for 5 minutes at 40–42° C. The dispersion is then cooled with stirring to room temperature (25° C.) so that the drops of phase A harden to form microcapsules. The microcapsules are isolated by decantation. In view of the adhering oil phase, however, the formulation obtained consists of an oily dispersion with a high solids content (phase A: 93% by weight, phase B: 7% by weight).

1b: Production of the hydrophobicized powder

| | Constituents | | % by weight |
|---|---|---|---|
| 8 | Microcapsule dispersion | from 1a | 75 |
| 9 | Polytrap ® 6603* | Acrylate copolymer | 25 |

\* Manufacturer: Advanced Polymer Systems, marketing: Dow Corning

The oily microcapsule dispersion is then mixed with Polytrap® 6603 until a homogeneous powder is obtained. The content of Photonyl® LS in the hydrophobicized powder is 20% by weight.

The invention claim is:

1. A process for making hydrophobicized powders of micro- and/or nanocapsules comprising:
   (a) providing an aqueous polymer solution containing at least one active ingredient and at least one hydrophilic polymer;
   (b) providing an oil component heated to a temperature above a gel point of the aqueous polymer solution;
   (c) dispersing (a) in (b) in the presence of a water-in-oil emulsifier to form a dispersion;
   (d) cooling the dispersion while mixing to a temperature below the gel point of the aqueous polymer solution to form micro- and/or nanocapsules containing the active ingredient encapsulated therein;
   (e) harvesting the micro- and/or nanocapsules from the dispersion to recover micro- and/or nanocapsules coated with oil; and
   (f) contacting the micro- andlor nanocapsules coated with oil with an oil-absorbing auxiliary ingredient, whereby, micro- and/or nanocapsules with a protective, hydrophobic coating comprising the oil-absorbing auxiliary ingredient is formed.

2. The process of claim 1 wherein the oil-absorbing auxiliary ingredient is employed in an amount of from about 5 to 35% by weight, based on the weight of the hydrophobicized powder.

3. The process of claim 1 wherein the oil-absorbing auxiliary ingredient is employed in an amount of from about 15 to 25% by weight, based on the weight of the hydrophobicized powder.

4. The process of claim 1 wherein the micro- and/or nanocapsules have a mean particle diameter of from about 0.1 to 500 µm.

5. The process of claim 1 wherein the process produces microcapsules having a mean particle diameter of from about 10 to 50 µm.

6. The process of claim 1 wherein the micro- and/or nanocapsules are harvested from the dispersion by decanting the oil from the dispersion to form a decanted dispersion containing the micro- and/or nanocapsules.

7. The process of claim 6 wherein the decanted dispersion has a residual oil content of from about 2 to 20% by weight, based on the weight of the decanted dispersion.

8. The process of claim 6 wherein the decanted dispersion has a residual oil content of from about 5 to 10% by weight, based on the weight of the decanted dispersion.

9. The process of claim 1 wherein the micro- and/or nanocapsules contain from about 0.1 to 50% by weight of active ingredient.

10. The process of claim 1 wherein the micro- and/or nanocapsules contain from about 5 to 10% by weight of active ingredient.

\* \* \* \* \*